United States Patent [19]

Zaiger

[11] Plant 4,339

[45] Dec. 5, 1978

[54] APRICOT TREE

[76] Inventor: C. Floyd Zaiger, 537 Rosemore Ave., Modesto, Calif. 95351

[21] Appl. No.: 862,633

[22] Filed: Dec. 20, 1977

[51] Int. Cl.[2] ..... A01H 5/03
[52] U.S. Cl. ..... Plt./39
[58] Field of Search ..... Plt./39

*Primary Examiner*—Robert E. Bagwill
*Assistant Examiner*—James R. Feyrer

[57] ABSTRACT

A variety of apricot tree of large size, vigorous growth and a regular, productive bearer of early maturing, large, firm, freestone fruit, with good shipping quality. The tree is further characterized by having a low winter chilling requirement.

4 Drawing Figures

ORIGIN OF THE VARIETY

The present variety of apricot tree originated by me in my experimental orchard located near Modesto, Stanislaus County, Calif., as a selected seedling from a large number of seedlings obtained from Flaming Gold apricot (U.S. Pat. No. 2,822) seeds that had resulted from open-pollinated flowers. These seedlings which were planted and grown under careful observation by me, gave the selected seedling, which is the present variety. I maintained the selection under careful and continual observation during which time I recognized its distinct and desirable characteristics described above and selected the variety for reproduction.

ASEXUAL REPRODUCTION OF THE VARIETY

Asexual reproduction of the new variety by budding as performed at Modesto, Calif., shows that said characteristics come true to form and are established and transmitted through succeeding propagations.

SUMMARY OF THE VARIETY

My present discovery relates to a new and distinct variety of apricot tree which is of large size, medium dense, upright growth. A productive and regular bearer of early ripening, firm, freestone fruit, of good eating and shipping quality.

The present variety of apricot tree when compared to its seed parent, Flaming Gold apricot, (U.S. Pat. No. 2,822) has more uniform distribution of fruit throughout the tree; a more uniform ripening of fruit throughout the tree; and has the ability to produce fruit in warmer winter areas by having a lower winter chilling requirement.

BRIEF DESCRIPTION OF THE DRAWING

The accompanying photographs show reproductions in color of the foliage and fruit of my new variety, with the upper and lower surface of the leaves being illustrated, also an exterior and a sectional view of the fruit being shown with the stone remaining in place therein. These illustrations were taken shortly after being picked at maturity (shipping ripe). The colors are as nearly true as is reasonably possible in a color representation of this type.

DESCRIPTION OF THE VARIETY

The following is a detailed description of my new variety, with color terminology, (except those in common color terms), in accordance with Reinhold Color Atlas by A. Korneruf and J. H. Wanscher:

Tree:
- *Size.*—Large.
- *Vigor.*—Vigorous.
- *Growth.*—Upright.
- *Density.*—Medium dense.
- *Production.*—Productive.
- *Bearer.*—Regular.

Trunk:
- *Size:.*—Stocky.

Branches:
- *Size.*—Medium.
- *Texture.*—Smooth to medium rough.
- *Color.*—New growth — Reddish brown. Old growth — Brown to grayish brown.
- *Lenticels.*—Numerous. Medium.

Leaves:
- *Size.*—Large. Average length — 3¾". Average width — 3¼".
- *Form.*—Ovate.
- *Thickness.*—Medium.
- *Margin.*—Serrate.
- *Petiole.*—Average length — 1⅜". Average width — 3/32".
- *Glands.*—Average number 3. Range 0–4. Primarily on petiole.
- *Color.*—Upper surface — dark green (28-F-8 to 29-F-8). Lower surface — grayish green (28-E-7 to 29-E-8).

Flowers:
- *Blooming period.*—Feb. 18, 1977 to Mar. 5, 1977 at Modesto, Calif. Varies from year to year due to weather variations.
- *Size.*—Medium to large.
- *Color.*—Varies from white to light pink.

Fruit:
- *Maturity.*—Shipping ripe — Last week of May. Eating ripe — The first week of June.
- *Size.*—Large. Average axial diameter — 2". Transverse diameter in suture plane from — 2" to 2¼". Average diameter transversely at right angles to the suture plane — 1¾" to 2".
- *Form.*—Spherical; nearly symetrical; suture is shallow but slightly more pronounced at stem and terminating at the blossom end.
- *Cavity.*—From rounded to somewhat elongated in suture plane from — 3/16" to ¼" deep.

*Base.*—Usually flat but torus like around the cavity.

*Apex.*—Rounded to slightly depressed: with pistil point slightly depressed.

Skin:

*Thickness.*—Medium.

*Tenacity.*—Tenacious to flesh.

*Texture.*—Smooth.

*Tendency to crack.*—None.

*Color.*—Ground color near light orange (5-A-8) with a major portion of skin covered with a light orange-red blush (8-B-8).

*Down.*—Scant. Very short.

Flesh:

*Color.*—From light orange (6-A-6) to persian orange (6-A-7).

*Flavor.*—Predominantly apricot.

*Juice.*—Moderate.

*Fibers.*—Medium size. Tender.

*Ripens.*—Evenly.

*Eating quality.*—Good.

Stone:

*Type.*—Free. Adheres slightly to flesh along ventricle edge.

*Size.*—Medium to large. Length — from 1⅛" to 1¼" Breadth — 1" to 1⅛" Thickness — ½" to ⅝".

*Form.*—Ovoid. Very slightly cuneate toward apex.

*Ridges.*—Sharp ridges extending across the surface of the stone on both sides of suture plane.

*Tendency to split.*—None.

*Surface.*—Regularly pitted, only slightly throughout.

*Color.*—Varies slightly from light brown (5-D-6) to golden brown (5-D-5).

Use: Dessert. Market — local and long distance shipping.

Keeping quality: Good.

Shipping quality: Good.

The apricot tree and its fruit herein described may vary in slight detail due to climatic and soil conditions under which the variety may be grown; the present botanical description being of the variety as grown near Modesto, Stanislaus County, Calif. With the exception of winter chilling requirement, which was evaluated by me at the test orchard located in the Imperial Valley at Calipatria, Calif.

I claim:

1. A new and distinct variety of apricot tree, substantially as herein shown and described, characterized particularly as to novelty by its ability to be a regular and productive bearer of large fruit of good commercial quality in warm winter areas, by having a low winter chilling requirement, the tree is further characterized by its even distribution of fruit throughout the tree and its uniform ripening of large, firm, freestone fruit of good eating and shipping quality.

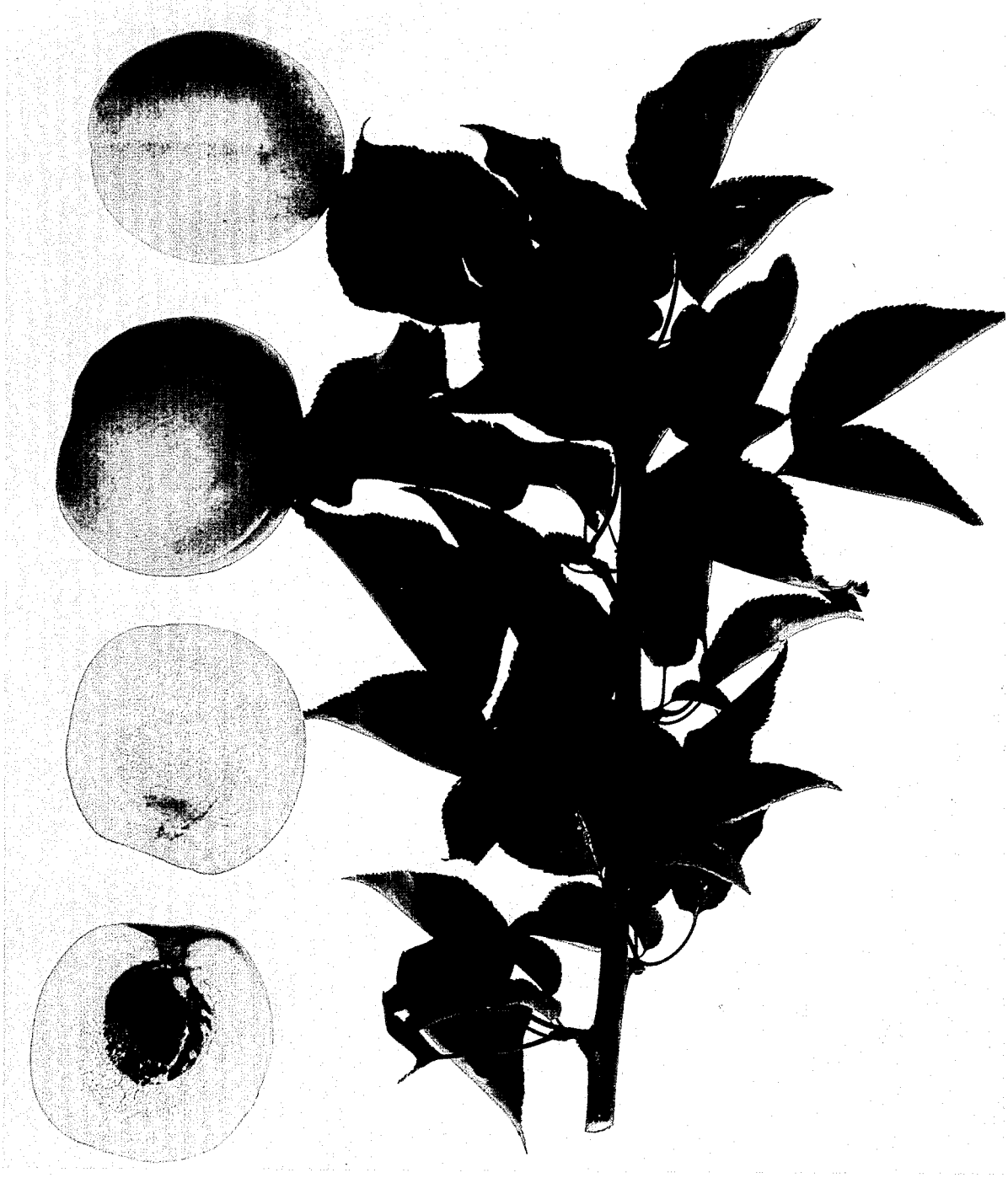

* * * * *